United States Patent
Auweter et al.

(10) Patent No.: US 7,105,176 B2
(45) Date of Patent: Sep. 12, 2006

(54) PRODUCTION OF SOLID PREPARATIONS OF WATER-SOLUBLE, SPARINGLY WATER-SOLUBLE OR WATER-INSOLUBLE ACTIVE COMPOUNDS

(75) Inventors: Helmut Auweter, Limburgerhof (DE); Heribert Bohn, Wattenheim (DE); Erik Lüddecke, Mutterstadt (DE); Willy Hinz, Mannheim (DE); Frank Runge, Friedelsheim (DE); Angelika-Maria Pfeiffer, Birkenheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 207 days.

(21) Appl. No.: 09/988,109

(22) Filed: Nov. 19, 2001

(65) Prior Publication Data

US 2002/0110599 A1 Aug. 15, 2002

(30) Foreign Application Priority Data

Nov. 29, 2000 (DE) .................. 100 59 213
Jun. 22, 2001 (DE) .................. 101 29 713

(51) Int. Cl.
*A61K 47/00* (2006.01)
*A61K 9/00* (2006.01)
*A61K 9/28* (2006.01)
*A61K 9/14* (2006.01)
*A61K 9/50* (2006.01)

(52) U.S. Cl. ............ 424/439; 424/400; 424/441; 424/442; 424/484; 424/489; 424/499; 424/500

(58) Field of Classification Search ........... 424/400, 424/439, 441, 442, 484, 489, 499, 500
See application file for complete search history.

(56) References Cited

U.S. PATENT DOCUMENTS 4,522,743 A * 6/1985 Horn et al.
5,658,377 A * 8/1997 Craig
5,968,251 A 10/1999 Auweter et al. ............ 106/498
2003/0185877 A1 10/2003 Betz et al. .................. 424/442

FOREIGN PATENT DOCUMENTS

| DE | 1 211 911 | 3/1966 |
| DE | 199 17 751 | 11/2000 |
| EP | 0 065 193 | 11/1982 |
| EP | 0 410 236 | 1/1991 |
| EP | 0 444 323 | 9/1991 |
| EP | 0 498 824 | 8/1992 |
| EP | 0 556 883 | 8/1993 |
| EP | 498824 B1 * | 1/1994 |
| EP | 0 845 503 | 6/1995 |
| EP | 0 832 569 | 4/1998 |
| EP | 0 933 376 | 8/1999 |
| EP | 0 937 412 | 8/1999 |
| EP | 937412 A1 * | 8/1999 |
| GB | 393319 | 6/1933 |
| GB | 2 232 573 | 12/1990 |
| WO | WO 91/06292 | 5/1991 |
| WO | 93/10768 | 6/1993 |
| WO | WO 94/05645 | 3/1994 |
| WO | WO 94/19411 | 9/1994 |
| WO | WO 96/23420 | 8/1996 |
| WO | WO 98/26008 | 6/1998 |

OTHER PUBLICATIONS

Manz "Die Anwendung und Bedeutung von synthetischen Carotinoiden in der Lebens-und Futtermittel-sowie in der pharmazeutischen Industrie" Chimia No. 21 (1967) pp. 329-335.

* cited by examiner

*Primary Examiner*—Humera N. Sheikh
(74) *Attorney, Agent, or Firm*—Novak Druce & Quigg, LLP; Jason D. Voight

(57) ABSTRACT

A process is described for producing solid preparations of at least one water-soluble, sparingly water-soluble or water-insoluble active compound suitable for the food and animal feed sectors or for pharmaceutical and cosmetic applications. In addition, the invention relates to oily suspensions in which these preparations are present as disperse phase, and to the use of these preparations as additive to animal feeds, foods, pharmaceuticals and cosmetic preparations.

21 Claims, No Drawings

PRODUCTION OF SOLID PREPARATIONS OF WATER-SOLUBLE, SPARINGLY WATER-SOLUBLE OR WATER-INSOLUBLE ACTIVE COMPOUNDS

This application claims foreign priority to German Application No. 10059213.9 filed Nov. 29, 2000 and German Application No. 10129713.0 filed Jun. 22, 2001.

The invention relates to a process for producing solid preparations of at least one water-soluble, sparingly water-soluble or water-insoluble active compound suitable for the food and animal feed sectors or for pharmaceutical and cosmetic applications. In addition the invention relates to oily suspensions containing these preparations and to their use as additive to animal feeds, foods, pharmaceutical and cosmetic preparations.

Numerous active compounds suitable for the food and animal feed sectors or for pharmaceutical and cosmetic applications, for example fat-soluble vitamins, carotenoids, but also the natural pigments curcumin and carmine, because of their water insolubility and their sensitivity to oxidation, can only be used in the form of specially stabilized preparations. Direct use of the crystalline materials, inter alia, for coloring aqueous foods, as feed additives or as active compounds in cosmetic preparations is generally not possible. The high requirements with respect to bioavailability, coloring properties and dispersibility, in particular in aqueous media, but also in lipophilic media, can only be met by means of special formulations.

Satisfactory color yields may only be achieved in the case of direct coloring of foods by means of preparations in which the active compounds, for example carotenoids, are present in finely divided form and, if appropriate, are protected from oxidation by protecting colloids. These formulations used in animal feeds lead to a higher bioavailability of the active compounds and thus indirectly to improved coloring effects, for example in egg yolk pigmentation or fish pigmentation.

A number of very varied formulation processes are already known from the literature which all have the purpose of reducing the crystallite size of the active compounds and bringing it to a particle size range of less than 10 μm.

Numerous methods, described, inter alia, in Chimia 21, 329 (1967), WO 91/06292 and in WO 94/19411, make use of grinding carotenoids using a colloid mill and thus achieve particle sizes of from 2 to 10 μm.

In addition there are combined emulsification/spray-drying processes, as are described, for example, in DE-A-12 11 911 or in EP-A-0 410 236.

According to European patent EP-B-0 065 193, finely divided pulverulent carotenoid preparations are prepared by dissolving, for example, β-carotene in a volatile water-miscible organic solvent at temperatures from 50° C. to 200° C., possibly at elevated pressure, in the course of a period of less than 10 seconds. The β-carotene is precipitated out of the resultant molecular dispersion by immediate rapid mixing with an aqueous solution of a protecting colloid at from 0° C. to 50° C. This produces an orange-yellow colloidally disperse β-carotene hydrosol. Subsequent spray-drying of the dispersion produces a free-flowing dry powder which dissolves in water forming a clear yellow-orange dispersion.

A similar process for producing finely divided pulverulent carotenoid preparations is described in EP-A-0 937 412 which uses water-immiscible solvents.

WO 98/26008 relates to the use of a mixture of low-molecular-weight and high-molecular-weight protecting colloids for producing redispersible xanthophyll-containing dry powders.

Carotenoids are being used more and more in the form of liquid preparations as feed additives in animal nutrition. This has the advantage, inter alia, that metering can be simpler and more accurate. In addition, it is possible in what is termed post-pelleting application not to charge feed pellets until after their manufacture with a liquid preparation of feed additives. This means that even oxidation- and heat-sensitive additives such as carotenoids can be used without relatively great losses.

Examples of post-pelleting application (PPA) may be found, inter alia, in GB-A-2 232 573 and in EP-A-0 556 883 and the literature cited therein.

WO 96/23420 describes oily suspensions of crystalline astaxanthin of a particle size less than 2 μm. Suspensions of this type have been produced, inter alia, by grinding the astaxanthin crystals in oil. In addition, the publication comprises the use of suspensions for charging extruded feed after extrusion. However, the stability of such suspensions and the bioavailability of the astaxanthin present therein are not always sufficient for many applications.

carotenoid emulsions, as a specific form of a liquid formulation, frequently have the disadvantage that they are unstable physically (occurrence of phase separation) and chemically (occurrence of unwanted hydrolysis and/or redox reactions, chemical incompatibility of individual dissolved components) and, in addition, the danger of microbiological contamination can frequently occur.

In other processes, described in WO 94/19411, crystalline β-carotene, for example, is ground in the presence of an aqueous protecting colloid solution and is then converted into an amorphous modification by short-time heating to the melting point.

This formulation and the copiously described aqueous carotenoid dispersions and O/W emulsions which comprise the active compound in the presence of stabilizing protecting colloids are also unsuitable, since they are immiscible with oils.

EP-A-0 845 503 describes liquid oil-miscible carotenoid preparations which, as a double dispersion system, comprise an aqueous disperse phase having a particle diameter less than 100 μM in which the protecting colloid-stabilized particles of one or more carotenoids are present in disperse form in an oil as dispersion medium.

It is an object of the present invention to propose a process for producing solid preparations of water-soluble, sparingly water-soluble or water-insoluble active compounds. In addition, preparations having a high active compound concentration are to be made available.

It is also an object of the present invention to provide liquid, oil-miscible carotenoid formulations which are suitable, inter alia, in the animal nutrition sector for applying to feed pellets.

We have found that this object is achieved according to the invention by a process for producing solid preparations of at least one water-soluble, sparingly soluble or water-insoluble active compound suitable for the food and animal feed sectors or for pharmaceutical and cosmetic applications by a) dissolving or dispersing at least one of the abovementioned active compounds in an aqueous molecular dispersion or colloidal dispersion of a proteinaceous protecting colloid, b) flocculating the proteinaceous protecting colloid together with the active compound out of the dispersion and c) separating off the flocculated solid from the water and any solvents additionally used and subsequently converting them into a dry powder.

Active compounds which are suitable for the purposes of the present invention for the food and animal nutrition sectors or for pharmaceutical and cosmetic applications are, for example, the following compounds:

Fat-soluble vitamins, for example the K vitamins, vitamin A and derivatives such as vitamin A acetate, vitamin A propionate or vitamin A palmitate, vitamin $D_2$ and vitamin $D_3$ and also vitamin E and derivatives. Vitamin E in this context is natural or synthetic α, β, γ- or δ-tocopherol, preferably natural or synthetic α-tocopherol, and also tocotrienol. Vitamin E derivatives are, for example, tocopheryl-$C_1$–$_{20}$-carboxylic esters, such as tocopheryl acetate or tocopheryl palmitate.

Water-soluble vitamins, for example ascorbic acid and its salts such as sodium ascorbate and vitamin C derivatives such as sodium, calcium or magnesium ascorbyl-2-monophosphate or calcium ascorbyl-2-polyphosphate, calcium pantothenate, panthenol, vitamin $B_1$ (thiamine), as hydrochloride, nitrate or pyrophosphate, vitamin $B_2$ (riboflavin) and its phosphates, vitamin $B_6$ and salts, vitamin $B_{12}$, biotin, folic acid and folic acid derivatives such as tetrahydrofolic acid, 5-methyltetrahydrofolic acid, 5-formyltetrahydrofolic acid, nicotinic acid and nicotinamide.

Polyunsaturated fatty acids, for example linoleic acid, linolenic acid, arachidonic acid, eicosapentaenoic acid, docosahexaenoic acid.

Natural food pigments such as carotenoids, curcumin, carmine or chlorophyll.

Water-insoluble or sparingly water-soluble organic UV filter substances, for example compounds selected from the group consisting of triazines, anilides, benzophenones, triazoles, cinnamides and sulfonated benzimidazoles.

For cosmetic uses as light screens, active compounds are particularly 1,3,5-triazine derivatives of the formula I

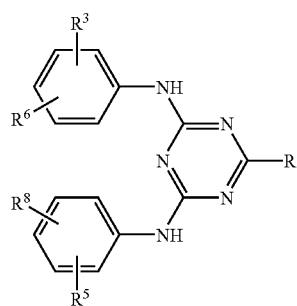

where the substituents independently of one another have the following meaning:

R is hydrogen, halogen, OH, $C_1$–$C_{20}$-alkyl, $C_1$–$C_{20}$-alkoxy, $C_1$–$C_{20}$-alkoxyalkyl, $C_1$–$C_{20}$-hydroxyalkoxy, $NR^1R^2$, or a radical of the formula Ia

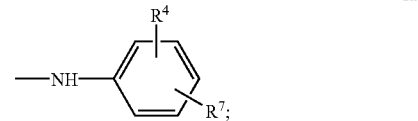

$R^1$ and $R^2$ are hydrogen, $C_1$–$C_{20}$-alkyl, $C_6$–$C_{12}$-aryl which may be substituted by one or more $C_1$–$C_4$-alkyl, $C_7$–$C_{10}$-aralkyl which may be substituted by one or more $C_1$–$C_4$-alkyl, heteroaryl which may be substituted by one or more $C_1$–$C_4$-alkyl, $C_5$–$C_8$-cycloalkyl;

$R^3$ to $R^5$ are hydrogen, OH, $NR^9R^{10}$, $C_1$–$C_{20}$-alkoxy, $C_6$–$C_{12}$-aryl which may be substituted by one or more $C_1$–$C_4$-alkyl, $C_7$–$C_{10}$-aralkyl which may be substituted by one or more $C_1$–$C_4$-alkyl, heteroaryl which may be substituted by one or more $C_1$–$C_4$-alkyl, $C_5$–$C_8$-cycloalkyl;

$R^6$ to $R^8$ are hydrogen, $C_1$–$C_{20}$-alkoxy, —C(=O)—$R^{11}$, —C(=O)—X—$R^{12}$, $SO_2R^{13}$, CN;

$R^9$ to $R^{11}$ are hydrogen, $C_1$–$C_{20}$-alkyl, $C_6$–$C_{12}$-aryl which may be substituted by one or more $C_1$–$C_4$-alkyl, $C_7$–$C_{10}$-aralkyl which may be substituted by one or more $C_1$–$C_4$-alkyl, heteroaryl which may be substituted by one or more $C_1$–$C_4$-alkyl, $C_5$–$C_8$-cycloalkyl;

$R^{12}$ is hydrogen, $C_1$–$C_{20}$-alkyl, $C_6$–$C_{12}$-aryl which may be substituted by one or more $C_1$–$C_4$-alkyl, $C_7$–$C_{10}$-aralkyl which may be substituted by one or more $C_1$–$C_4$-alkyl, heteroaryl which may be substituted by one or more $C_1$–$C_4$-alkyl, $C_5$–$C_8$cycloalkyl, or a radical of the formula Sp-Sil;

$R^{13}$ is $C_1$–$C_{20}$-alkyl, $C_5$–$C_8$-cycloalkyl, $C_6$–$C_{12}$-aryl which may be substituted by one or more $C_1$–$C_4$-alkyl, $C_7$–$C_{10}$-aralkyl which may be substituted by one or more $C_1$–$C_4$-alkyl, heteroaryl which may be substituted by one or more $C_1$–$C_4$-alkyl;

X is O, $NR^{14}$;

$R^{14}$ is hydrogen, $C_1$–$C_{20}$-alkyl, $C_6$–$C_{12}$-aryl which may be substituted by one or more $C_1$–$C_4$-alkyl, $C_7$–$C_{10}$-aralkyl which may be substituted by one or more $C_1$–$C_4$-alkyl, heteroaryl which may be substituted by one or more $C_1$–$C_4$-alkyl, $C_5$–$C_8$-cycloalkyl;

Sp is spacer;

Sil is a radical from the group consisting of silanes, oligosiloxanes and polysiloxanes.

Alkyl radicals for R, $R^1$ and $R^2$, and $R^9$ to $R^{14}$, are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, 1,1,3-trimethylhexyl, 1,1,3,3-tetramethylpentyl, n-nonyl, n-decyl, n-undecyl, 1-methylundecyl, n-dodecyl, 1,1,3,3,5,5-hexamethylhexyl, n-tridecyl, n-tetradecyl, n-pentadecyl, n-hexadecyl, n-heptadecyl, n-octadecyl, n-nonadecyl or n-icosyl.

Halogen for R is fluorine, bromine, iodine, or preferably chlorine.

Alkoxy radicals for R and $R^3$ to $R^8$ which come into consideration are straight-chain and branched radicals having from 1 to 20 carbons, preferably having from 1 to 12 carbons, particularly preferably having from 1 to 8 carbons.

For example they are:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Hydroxyalkoxy radicals which come into consideration for R are the abovementioned alkoxy radicals having an additional terminal hydroxyl function.

Cycloalkyl radicals for $R^1$ to $R^5$ and $R^9$ to $R^{14}$ are preferably branched or unbranched $C_3$–$C_{10}$-cycloalkyl radicals such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. Preference is given to $C_5$–$C_8$-cycloalkyl such as cyclopentyl, cycloheptyl, cyclooctyl, and in particular cyclohexyl.

The cycloalkyl radicals can be unsubstituted or substituted by one or more, for example 1 to 3, radicals such as halogen, for example fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or can contain, in the ring, 1 to 3 heteroatoms, such as sulfur, nitrogen whose free valences can be saturated by hydrogen or $C_1$–$C_4$-alkyl, or oxygen.

Examples of $C_6$–$C_{12}$-aryl are in particular phenyl, naphthyl and biphenyl.

Examples of $C_7$–$C_{10}$-aralkyl are benzyl, phenylethyl, α-methylphenylethyl and α,α-dimethylbenzyl.

Heteroaryl radicals are advantageously single or condensed aromatic ring systems having one or more heteroaromatic 3- to 7-membered rings. Heteroatoms which may be present in the ring or ring system are one or more nitrogen, sulfur and/or oxygen atoms.

Substituents of the abovementioned aryl, aralkyl and heteroaryl radicals which come into consideration are $C_1$–$C_4$-alkyl groups, for example methyl, ethyl, n-propyl, 1-methylethyl, n-butyl, 1-methylpropyl, 2-methylpropyl and 1,1-dimethylethyl.

The term spacer for Sp, in this context, means a bivalent branched or unbranched $C_3$–$C_{12}$-alkylene or -alkenylene chain which links the silane, oligosiloxane or polysiloxane moiety to the triazine radical.

Examples of a $C_3$–$C_{12}$-alkylene chain are propylene, 2-methylpropylene, butylene, pentylene and hexylene.

Examples of a $C_3$–$C_{12}$-alkenylene chain are 2-propen-2-ylene, 2-methyl-3-propenylene, 3-buten-3-ylene and 4-penten-4-ylene.

Preferred spacers are —(CH$_2$)$_3$—, —(CH$_2$)$_4$—, —(CH$_2$)$_5$—, —[CH(CH$_3$)]—(CH$_2$)—, —(CH$_2$)$_2$—CH=CH—, —C(=CH$_2$)—CH$_2$—, —C(=CH$_2$)—(CH$_2$)$_2$—O—(CH$_2$)$_4$—, —(CH$_2$)$_4$—O—(CH$_2$)$_2$—.

The term silanes in this context is a radical $SiR^{15}R^{16}R^{17}$, where $R^{15}$, $R^{16}$, $R^{17}$ independently of one another are $C_1$–$C_6$-alkyl, $C_1$–$C_6$-alkoxy or phenyl.

Examples are: Si(CH$_2$—CH$_3$)$_3$, Si(CH$_2$—CH$_2$—CH$_3$)$_3$, Si(isopropyl)$_3$, Si(tert-butyl)$_3$, Si(tert-butyl)(CH$_3$)$_2$, Si(CH$_3$)$_2$-(hexyl), Si(OCH$_3$)$_3$, Si(OEt)$_3$, SiPh$_3$.

The term oligosiloxanes is a radical selected from the group of the general formula consisting of SiR$^{18}_m$(OSiR$^{18}_3$)$_n$ where m=0, 1 or 2; n=3, 2 or 1 and m+n=3, $R^{18}$—[Si($R^{18}$)$_2$—O—]$_r$—Si($R^{18}$)$_2$—A and $R^{18}$—[Si($R^{18}$)$_2$—O—]$_r$—Si(A)($R^{18}$)—O—Si($R^{18}$)$_3$, where A is a chemical bond or a spacer and $R^{18}$ is a $C_1$–$C_6$-alkyl radical or a phenyl radical and r has values of from 1 to 9.

The term polysiloxanes comprises, for example, a radical selected from the group of the general formula consisting of A—[Si($R^{19}$)$_2$—O ]$_s$—Si($R^{19}$)$_2$—A or ($R^{19}$)$_3$—Si—[O—Si($R^{19}$)$_2$]]$_t$—[O—Si($R^{19}$)—(A)]$_q$—O—Si($R^{19}$)$_3$, where A is a chemical bond or a spacer and $R^{19}$ is a $C_1$–$C_6$-alkyl radical or phenyl radical, s and t have values of from 4 to 250 and q has values from 1 to 30.

Examples of silanyltriazines where $R^{12}$ is a radical of the formula Sp-Sil may be found in EP-A-0 933 376.

In the foreground are triazine compounds of the formula Ib,

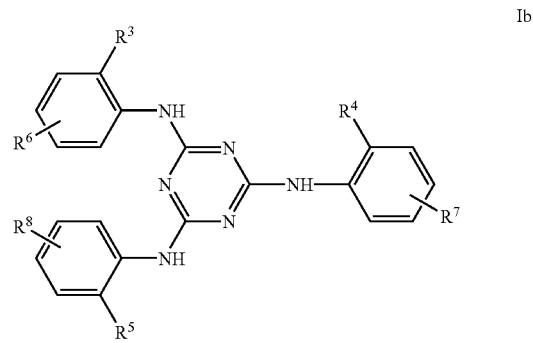

where $R^3$ to $R^5$ are in the ortho position to the phenylamino radical of the triazine.

Preference for use as light screen is given to dry powders comprising at least one 1,3,5-triazine derivative of the formula Ib where the substituents independently of one another have the following meaning:

$R^3$ to R5 hydrogen, OH;

$R^6$ to $R^8$ $C_1$–$C_{12}$-alkoxy, —C(=O)—X—$R^{12}$;

X O, $NR^{14}$;

$R^{12}$ and $R^{14}$ hydrogen, $C_4$–$C_8$-alkyl.

A particularly advantageous UVB filter is 2,4,6-trianilino-p-(carbo-2'-ethylhexyl-1'-oxy)-1,3,5-triazine, which is marketed by BASF Aktiengesellschaft under the trade name Uvinul® T150.

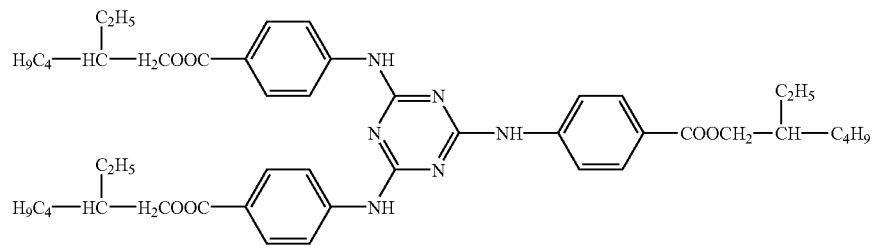
Uvinul® T150 is distinguished by good UV absorption properties with an extremely high extinction coefficient>1500 at 314 nm.
Further sparingly water-soluble or water-insoluble organic UV filter substances from the group of the triazines include the following compounds described in WO 94/05645 and EP-A-0 444 323:
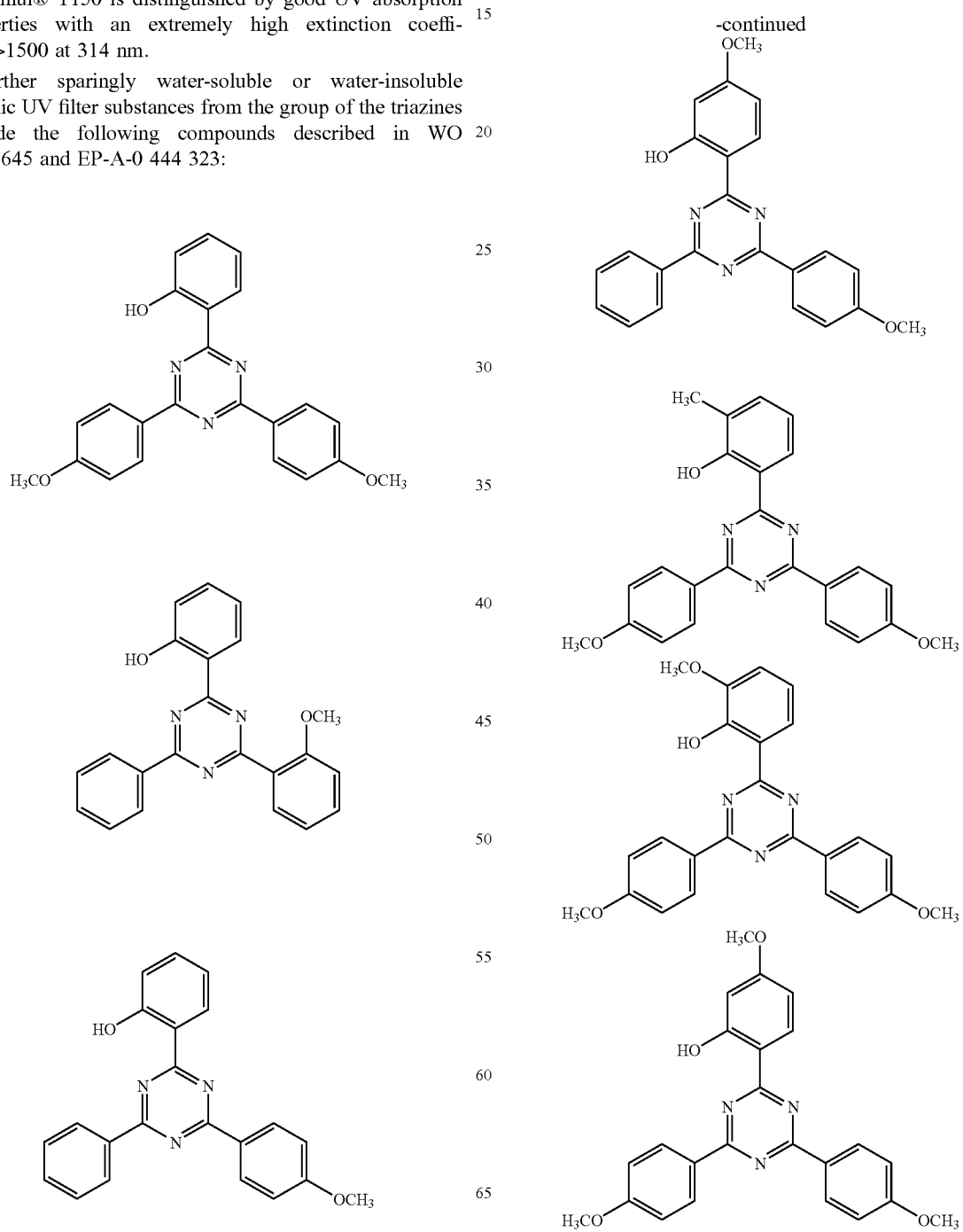

-continued
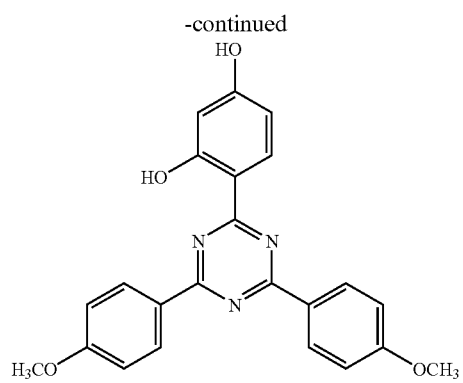
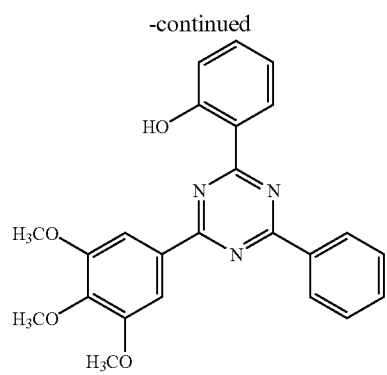
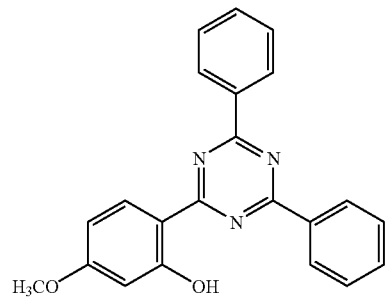
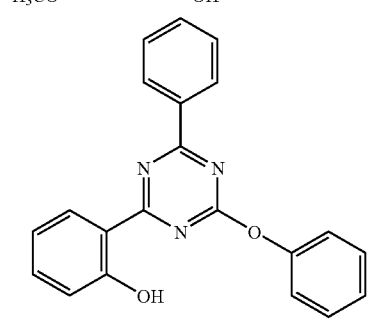
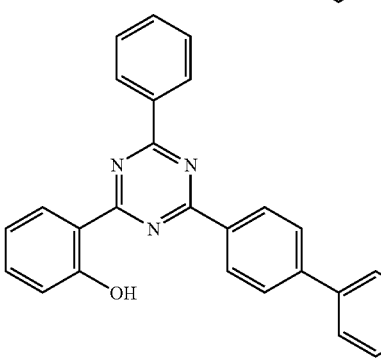
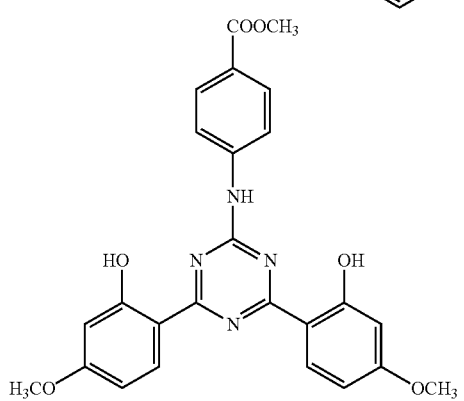

-continued

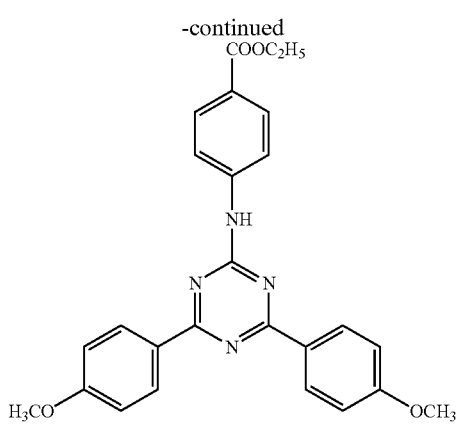

Preferred anilides are compounds of the formula II, where $W^1$ and $W^2$ independently of one another are $C_1$–$C_{18}$-alkyl or $C_1$–$C_{18}$-alkoxy.

II

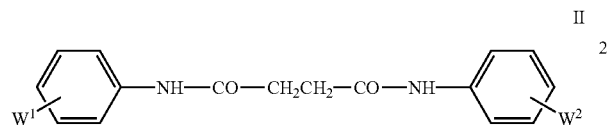

Particular preference is given to N-(2-ethoxyphenyl)-N'-(2-ethylphenyl)ethanediamide.

Preferred triazoles are compounds of the formula III in which, independently of one another, $T^1$ is $C_1$–$C_{18}$-alkyl or hydrogen and $T^2$ and $T^3$ are $C_1$–$C_{18}$-alkyl.

III

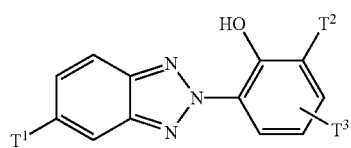

A further preferred compound class of water-insoluble triazoles are compounds of the formula IIIa where $T^4$ and $T^5$ independently of one another are $C_1$–$C_{18}$-alkyl.

IIIa

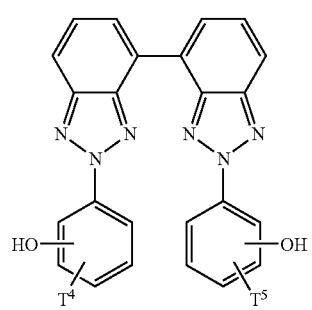

Representatives of the group of water-insoluble triazoles which are also preferred are compounds of the formulae IIIb and IIIc where $T^6$ and $T^7$ independently of one another are $C_1$–$C_{18}$-alkyl, preferably tert-butyl, —$(CH_3)_2$—$CH_2$—$C(CH_3)_3$ or 2-ethylhexyl. In the case of the particularly preferred compound of the formula IIIa, both radicals $T^6$ and T7 are —$(CH_3)_2$—$CH_2$—$C(CH_3)_3$. $T^8$ in the formula IIIc is also $C_1$–$C_{18}$-alkyl, preferably methyl.

IIIb

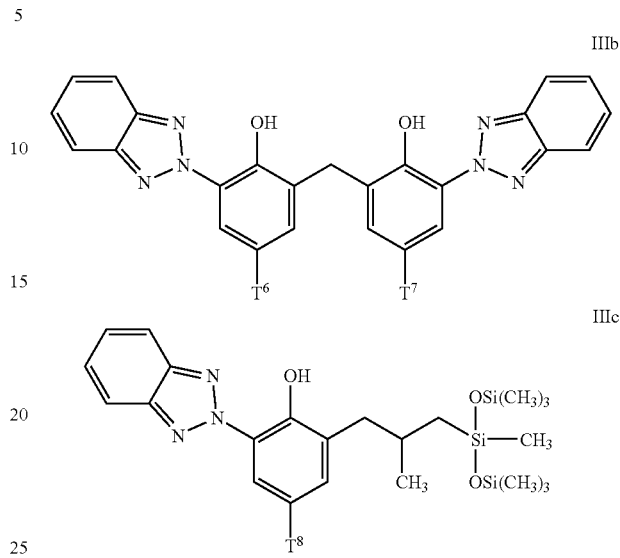

IIIc

Preferred cinnamides are compounds of the formula IV where independently of one another $Y^1$ and $Y^2$ are hydrogen or $C_1$–$C_4$-alkyl, preferably methyl or ethyl and $Y^3$ is aryl, preferably phenyl or 4-methoxyphenyl.

IV

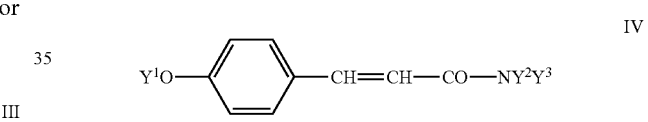

Preferred sulfonated benzimidazoles are compounds of the formula V where M is hydrogen, an alkali metal, preferably sodium, or an alkaline earth metal such as magnesium, calcium or zinc.

V

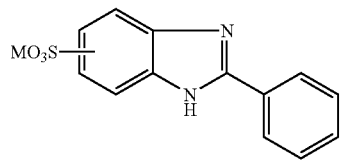

Preferred benzophenones are compounds of the formula VI where independently of one another $M^1$ to $M^4$ are hydrogen or $C_1$–$C_4$-alkyl, $M^1$ and $M^4$ are preferably methyl or ethyl and $M^2$ and $M^3$ are preferably hydrogen.

VI

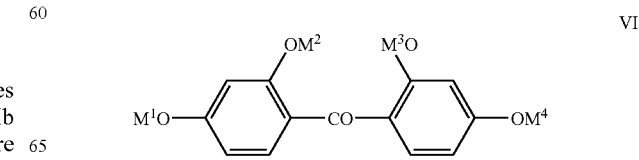

Further water-soluble, sparingly water-soluble or water-insoluble active compounds are minerals, amino acids, proteins or enzymes.

Minerals can be, for example, iron sulfate, zinc sulfate, manganese sulfate, copper sulfate, calcium sulfate, sodium sulfate, copper oxide, magnesium oxide, calcium fluoride, potassium chloride, potassium iodide, sodium chloride, calcium iodate, calcium phosphate, magnesium phosphate, potassium phosphate, sodium phosphate or iron phosphate, cobalt carbonate, sodium selenate or silicic acid and its salts. The amount of minerals used, for example in the animal nutrition sector, depends in each case on the requirements of the animals to be fed.

Amino acids can be in general all known physiologically compatible α-amino acids. Preferably these are alanine, arginine, asparagine, aspartic acid, cysteine, cystine, glutamine, glutamic acid, glycine, histidine, isoleucine, leucine, lysine, methionine, phenylalanine, hippuric acid, serine, and taurine. Particular preference is given to lysine, methionine and cysteine.

Enzymes in this context are preferably phosphatases, glucanases and if appropriate esterases or lipases, the latter in encapsulated form.

Other active compounds can be:

Compounds having vitamin or coenzyme character, for example choline chloride, carnitine, γ-butyrobetaine, lipoic acid, creatine, ubiquinones, S-methylmethionine, S-adenosylmethionine.

Feed antibiotics for medicated feed and microorganisms for improving digestion.

Water-insoluble active compounds in this context are those compounds whose water solubility at 20° C. is less than 0.05% by weight, preferably less than 0.01% by weight.

Sparingly water-soluble active compounds are those compounds whose water solubility at 20° C. is less than 5% by weight, preferably less than 1% by weight, particularly preferably less than 0.5% by weight, very particularly preferably from 0.5 to 0.05% by weight.

Water-soluble active compounds in this context are those compounds whose water solubility at 20° C. is greater than 5% by weight, preferably greater than 10% by weight, particularly preferably greater than 20% by weight, very particularly preferably greater than 60% by weight.

Preference is given to a process for producing solid preparations of at least one sparingly water-soluble or water-insoluble active compound suitable for the food and animal feed sectors or for pharmaceutical and cosmetic applications by dispersing, in process step a), at least one of the abovementioned sparingly water-soluble or water-insoluble active compounds in an aqueous molecular dispersion or colloidal dispersion of a proteinaceous protecting colloid.

The term dispersion is particularly preferably the production of aqueous suspensions and aqueous emulsions. Very particularly preferably dispersion step a) is the production of a suspension of at least one of the abovementioned solid active compounds in an aqueous molecular dispersion or colloidal dispersion of a proteinaceous protecting colloid in which the disperse phase comprises at least one of the active compounds as nanoparticulate particles.

Proteinaceous protecting colloids which are suitable according to the invention are not only water-soluble but also water-swellable proteins of animal or plant origin. Preferred protecting colloids are casein, caseinate, beef gelatin, pork gelatin or fish gelatin, in particular acid- or base-degraded gelatin having Bloom numbers in the range from 0 to 250, for example gelatin A 100, A 200, B 100 and B 200 and low-molecular-weight, enzymatically degraded gelatin types having a Bloom number of 0 and molecular weights of from 15,000 to 25,000 D, for example Collagel A and Gelitasol P (Stoess, Eberbach) and mixtures of these gelatin types. In some cases, however, milk powder, whole milk or skimmed milk are suitable as protecting colloids. Typical representatives of plant proteins are gluten, zein, soybean protein and pea protein. Particularly preferred protecting colloids are casein and caseinate.

For further details on the abovementioned protecting colloids, see R. A. Morton, Fat Soluble Vitamins, Intern. Encyclopedia of Food and Nutrition, Vol. 9, Pergamon Press 1970, pp. 128–131.

The water solubility or water swellability of the abovementioned polymers is dependent on temperature, pH and ionic strength of the solution.

The term flocculating out means those processes in a colloidal system which cause deposition, in the form of flakes, of the particles dispersed in this system and thus cause the sol/gel transition. Particles can generally be flocculated out by adding flocculation aids, electrolytes, polyelectrolytes, colloids of opposite charge or by heating and thus by denaturing the protein. An advantageous method for flocculating out the proteinaceous protecting colloid in process step b) features setting the pH of the dispersion to a value in the range of the isoelectric point of the protein used as protecting colloid. This range comprises according to the invention one pH unit above and below the isoelectric point, preferably 0.5 pH units, particularly preferably from 0.1 to 0.2 pH units. Very particularly preferably, the flocculation is initiated by setting the pH of the dispersion to a value corresponding to the isoelectric point of the protein used as protecting colloid.

The solid which has flocculated out can be separated off from the water and from any additionally used organic solvents in a manner known per se, for example by filtration or centrifugation.

The material can be converted into a dry powder, inter alia, by spray-drying, freeze-drying or drying in a fluidized bed, possibly also in the presence of a coating material. Suitable coating materials are, inter alia, corn starch, silicic acid or tricalcium phosphate.

During the lyophilization of the separated solid, cryoprotective substances can be added, for example trehalose or polyvinylpyrrolidones.

A preferred embodiment of the abovementioned process is that the suspension produced in process step a) is ground before the flocculation. In this case, the active compound is preferably suspended in crystalline form before the grinding operation.

The grinding can be performed in a manner known per se, for example using a ball mill. Depending on the type of mill used, grinding is continued until the particles have a mean particle size D[4.3], determined via Fraunhofer diffraction, of from 0.1 to 100 μm, preferably from 0.2 to 50 μm, particularly preferably from 0.5 to 30 μm, very particularly preferably from 0.8 to 20 μm, in particular from 1.0 to 10 μm. The term D[4.3] denotes the volume-weighted mean diameter (see handbook on the Malvern Mastersizer S, Malvern Instruments Ltd., UK).

Further details on grinding and the equipment used therefor may be found, inter alia, in Ullmann's Encyclopedia of Industrial Chemistry, Sixth Edition, 1999, Electronic Release, Size Reduction, Chapter 3.6.: Wet Grinding, and in EP-A-0 498 824.

A variant of the inventive process which is also preferred is that the dispersion in stage a) comprises the following steps:

a₁) dissolving one or more of the abovementioned active compounds in a water-miscible organic solvent or a mixture of water and a water-miscible organic solvent, or a₂) dissolving one or more of the abovementioned active compounds in a water-immiscible organic solvent and a₃) mixing the solution obtained by a₁) or a₂) with an aqueous molecular dispersion or colloidal dispersion of a proteinaceous protecting colloid, the hydrophobic phase of the active compound being produced as nanodisperse phase.

The water-miscible solvents used in stage a₁) are primarily water-miscible, thermally stable, volatile solvents which only contain carbon, hydrogen and oxygen, such as alcohols, ethers, esters, ketones and acetals. Expediently, those solvents are used which are at least 10% water-miscible, have a boiling point below 200° C. and/or have less than 10 carbons. Particularly preferably, methanol, ethanol, n-propanol, isopropanol, 1,2-butanediol 1-methyl ether, 1,2-propanediol 1-n-propyl ether, tetrahydrofuran or acetone is used.

The term "a water-immiscible organic solvent" for the purposes of the present invention is an organic solvent having a water solubility at atmospheric pressure of less than 10%. Possible solvents which come into consideration here are, inter alia, halogenated aliphatic hydrocarbons, for example methylene chloride, chloroform and carbon tetrachloride, carboxylic esters such as dimethyl carbonate, diethyl carbonate, propylene carbonate, ethyl formate, methyl, ethyl or isopropyl acetate, and ethers such as methyl tert-butyl ether. Preferred water-immiscible organic solvents are the following compounds selected from the group consisting of dimethyl carbonate, propylene carbonate, ethyl formate, ethyl acetate, isopropyl acetate and methyl tert-butyl ether.

When a water-immiscible solvent is used in accordance with process step a₂), it can be advantageous to free the dispersion obtained after process step a₃) from the water-immiscible solvent, for example by distillation, before the protein is flocculated out in step b).

The inventive process, in addition, is preferably the preparation of carotenoid-containing dry powders.

Particularly preferred carotenoid-containing dry powders according to the invention are those which comprise the following active compounds, selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin.

In the very particularly preferred production process for the abovementioned carotenoid-containing dry powders a) one or more carotenoids are dissolved in a water-miscible organic solvent, or a mixture of water and a water-miscible organic solvent, at temperatures above 30° C., b) the resultant solution is mixed with an aqueous casein solution or caseinate solution, c) the casein or caseinate is flocculated out of the dispersion together with the carotenoid at a pH of the dispersion which is in the region of the isoelectric point of casein or caseinate, d) the flocculated solid is separated off from the water and solvent and dried.

The abovementioned carotenoid-containing preparations are generally prepared in such a manner that at least one carotenoid is dissolved in a water-miscible organic solvent at temperatures above 30° C., preferably from 50° C. to 240° C., in particular from 100° C. to 200° C., particularly preferably from 140° C. to 180° C., if appropriate under pressure.

Since the action of high temperatures under some circumstances can decrease the desired high proportion of all-trans isomers, the carotenoid(s) is(are) dissolved as rapidly as possible, for example in a matter of seconds, for example in from 0.1 to 10 seconds, particularly preferably in less than 1 second. For rapid production of the molecular dispersion, the use of elevated pressure, for example in the range from 20 bar to 80 bar, preferably from 30 to 60 bar, can be advantageous.

The resultant molecular dispersion is then added directly with the possibly cooled aqueous molecular dispersion or colloidal dispersion of casein or caseinate in such a manner that a mixture temperature of about 35° C. to 80° C. is set.

The solvent component is transferred to the aqueous phase and the hydrophobic phase of the carotenoid(s) forms the nanodisperse phase.

For a more detailed description of the process and apparatus for the abovementioned dispersion, reference is made at this point to EP-B-0 065 193.

The casein or caseinate is flocculated out in process step c), in particular at a pH of the dispersion in the range from 4.0 to 5.5, preferably in the range from 4.4 to 5.2, particularly preferably in the range from 4.6 to 5.0, very particularly preferably in the range from 4.7 to 4.9. Most preferably, the casein or caseinate is flocculated out at pH 4.8.

Advantageous protecting colloids are low-molecular-weight and/or high-molecular-weight casein or caseinate or mixtures thereof. Preferably, Na caseinate having a molecular weight of 10,000 to 100,000 is used, particularly preferably having an MW of from 20,000 to 60,000, for example Na caseinate from Lacto Bretagne Associés S. A. (France) having an MW of approximately 38,000.

Details of the casein/caseinate used may be found, inter alia, in Ullmann's Encyclopedia of Industrial Chemistry, 6$^{th}$ Edition, 1998 Electronic Release, Chapter 11.1., Wiley V C H, Weinheim, Germany and in C D Römpp Chemie Lexikon [Römpp's Chemistry Lexicon] Version 1.0, Stuttgart/New York: Georg Thieme Verlag 1995 and the literature cited therein.

To increase the mechanical stability of the end product, it can be expedient in some cases to add a plasticizer to the colloid, such as sugars or sugar alcohols, for example sucrose, glucose, lactose, invert sugar, sorbitol, mannitol or glycerol.

To increase the stability of the active compound to oxidative degradation, it is advantageous to add stabilizers such as α-tocopherol, tertiary butylated hydroxytoluene, tertiary butylated hydroxyanisole, ascorbic acid or ethoxyquin. They can be added to either the aqueous or solvent phase, but preferably they are dissolved together with the active compounds in the solvent phase.

Under some circumstances it can also be advantageous to dissolve additionally in the solvent phase a physiologically approved oil, for example sesame oil, corn oil, cottonseed oil, soybean oil or peanut oil and esters of medium-chain plant fatty acids in a concentration of from 0 to 500% by weight, preferably from 10 to 300% by weight, particularly preferably from 20 to 100% by weight, based on the active compound(s), which is then precipitated out extremely finely divided together with the active compounds and said additives on mixing with the aqueous phase.

The invention also relates to solid preparations of at least one of the abovementioned water-soluble, sparingly water-soluble or water-insoluble active compounds suitable for the food and animal feed sectors or for pharmaceutical and cosmetic applications and obtainable by one of the processes mentioned at the outset.

Preference is given here to solid preparations comprising at compound suitable for the food and animal feed sectors or for pharmaceutical and cosmetic applications.

The active compound content in the inventive dry powders is in the range from 0.1 to 80% by weight, preferably from 1.0 to 75% by weight, particularly preferably from 5.0 to 70% by weight, very particularly preferably in the range from 20 to 65% by weight.

Preferred solid preparations in this context are carotenoid-containing dry powders, in particular those dry powders containing carotenoids and selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin.

In aqueous systems, outside the pH of the isoelectric point of the proteinaceous protecting colloid used, the inventive solid preparations can be redispersed again without any problems.

The inventive dry powders are suitable, in particular, as additive to foods and animal feeds and as additive to cosmetic and pharmaceutical preparations. Typical fields of application for the carotenoid-containing dry powders in the animal feed sector are, for example, fish pigmentation in aquaculture and pigmentation of egg yolks and broiler skin in poultry breeding.

For the abovementioned use, the dry powders are advantageously used in the form of oily suspensions.

The present invention thus also relates to oily suspensions comprising, as disperse phase, at least one water-soluble, sparingly water-soluble or water-insoluble active compound which is enclosed by one or more protecting colloids and is suitable for the food and animal feed sectors or for pharmaceutical and cosmetic applications, with the proviso that the oily suspensions do not comprise water-soluble vitamins.

The abovementioned water-soluble vitamins are, in particular, ascorbic acid and its salts such as sodium ascorbate and vitamin C derivatives such as sodium, calcium or magnesium ascorbyl-2-monophosphate or calcium ascorbyl-2-polyphosphate, calcium pantothenate, pantothenol, vitamin $B_1$ (thiamine), as hydrochloride, nitrate or pyrophosphate, vitamin $B_2$ (riboflavin) and its phosphates, vitamin $B_6$ and salts, vitamin $B_{12}$, biotin, folic acid and folic acid derivatives such as tetrahydrofolic acid, 5-methyltetrahydrofolic acid, 5-formyltetrahydrofolic acid, nicotinic acid and nicotinamide.

A preferred embodiment of the inventive oily suspensions is that they comprise, as disperse phase, solid preparations of at least one water-soluble, sparingly water-soluble or water-insoluble active compound suitable for the food and animal feed sectors or for pharmaceutical and cosmetic applications which are obtainable by a) dissolving or dispersing at least one of the abovementioned active compounds in an aqueous molecular dispersion or colloidal dispersion of a proteinaceous protecting colloid,
b) flocculating the proteinaceous protecting colloid together with the active compound out of the dispersion and
c) separating off the flocculated solid from the water and any solvents additionally used and subsequently converting them into a dry powder.

Preference is also given to those oily suspensions which comprise at least one carotenoid as active compound.

The carotenoids that can be used in the context of the invention are the known representatives of this class of substances accessible from natural sources or synthetically.

These are, for example, the following compounds: β-carotene, lycopene, lutein, astaxanthin, zeaxanthin, cryptoxanthin, citranaxanthin, canthaxanthin, echinenone, bixin, β-apo-4-carotenal, β-apo-8-carotenal, β-apo-8-carotenic esters, individually or as a mixture. Preference is given to at least one carotenoid from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin. Particularly preferred carotenoids are astaxanthin and canthaxanthin, very particular preference is given to astaxanthin.

As protecting colloids, the disperse phase, in addition to the abovementioned proteinaceous compounds, for example gelatin such as beef gelatin, pork gelatin or fish gelatin, gelatin hydrolyzates, casein, caseinate, whey protein and plant proteins, can also comprise starch, dextrin, pectin, gum arabic, modified starch, for example Na octenyl succinate starch, high-amylose starch (for example Hylon®, National Starch), individually or as mixtures. Typical representatives of plant proteins are gluten, zein, soybean proteins, rice proteins, potato proteins and pea proteins. However, polyvinyl alcohol, polyvinyl pyrrolidone, methyl cellulose, carboxymethyl cellulose, hydroxypropyl cellulose and alginates can also be used. Preferred protecting colloids are at least one proteinaceous protecting colloid selected from the group consisting of casein, caseinate, soybean protein, soybean protein hydrolyzates, pig gelatin and fish gelatin, or a modified starch.

For further details on the abovementioned protecting colloids, see R. A. Morton, Fat Soluble Vitamins, Intern. Encyclopedia of Food and Nutrition, Vol. 9, Pergamon Press 1970, pp. 128–131.

To improve their properties, the protecting colloids can be combined with emulsifiers.

The inventive oily formulations, in particular the carotenoid-containing oily suspensions, are distinguished, inter alia, in that they have a water content of from 0.1 to 6% by weight, preferably from 0.2 to 4% by weight, particularly preferably from 0.5 to 3% by weight.

The mean particle size D[4.3] of the disperse phase of the oily suspensions is in the range from 0.1 to 100 μm, preferably from 0.2 to 50 μm, particularly preferably from 0.5 to 30 μm, very particularly preferably from 0.8 to 20 μm, in particular in the range from 1.0 to 10 μm. The term D[4.3] denotes, in this context, the volume-weighted mean diameter (see handbook on the Malvern Mastersizer S, Malvern Instruments Ltd., UK).

In the preferred carotenoid-containing oily suspensions, at least one carotenoid is present in amorphous or partially amorphous form. The proportions of carotenoids present in the amorphous form, determined from x-ray diffraction diagrams, are in the range from 30 to 100%, preferably in the range from 40 to 99%, particularly preferably from 60 to 98%, very particularly preferably in the range from 70 to 95%.

Owing to the high degree of amorphousness of the active compounds, especially the carotenoids, in the oily suspensions, these formulations exhibit a particularly high bioavailability, linked with very good color yield in the pigmenting, for example, of egg yolks or fish, for example salmon.

The content of active compounds in the oily suspensions is generally from 0.1 to 50% by weight, preferably from 0.2 to 30% by weight, particularly preferably from 0.5 to 20% by weight, very particularly preferably from 1.0 to 15% by weight, based on the total amount of the oily suspension.

The dispersion medium used can be solid or liquid at 20° C. and can be not only of synthetic, mineral or plant origin, but also of animal origin. Typical representatives are, inter alia, sesame oil, corn oil, cottonseed oil, soybean oil or peanut oil, esters of medium-chain plant fatty acids, edible tallow, oleostearin and paraffin oil, glyceryl stearate, isopropyl myristate, diisopropyl adipate, 2-ethylhexanoic acid cetyl stearyl ester, hydrogenated polyisobutene, Vaseline, caprylic acid/capric acid triglycerides, microcrystalline wax, lanolin and stearic acid.

Preference is given in this context to edible oils that are liquid at 20° C., such as sunflower oil, palm oil, sesame oil, corn oil, cottonseed oil, soybean oil or peanut oil, esters of medium-chain triglycerides and, in addition, fish oils, for example mackerel oil, sprat oil or salmon oil. Those which are particularly preferred for animal nutrition are fish oils, corn oil, sunflower oil, soybean oil and peanut oil. Those which are additionally advantageous for the food/pharmaceutical sectors are the esters of medium-chain triglycerides.

Depending on the dispersion medium used (oil or hard fat), the inventive suspensions can be either in free-flowing form as a solid/liquid system or, depending on their viscosity and the melting point of the dispersion medium, can be in solid form, that is to say as heterogeneous solid/solid system.

To avoid sedimentation of the carotenoid-containing particles in the oily preparations, for example in the case of relatively long storage, in some cases the abovementioned hard fats (for example edible tallow or oleostearin) are also preferred as dispersion medium.

The amount of the dispersion medium is generally from 20 to 99.9% by weight, preferably from 50 to 99% by weight, particularly preferably from 55 to 97% by weight, very particularly preferably from 60 to 99% by weight, based on the total mass of the oily suspension.

In some cases it may be necessary for the oily suspensions to contain in addition aids, for example thickeners, hard fats, chelating agents, for example alkali metal salts or alkaline earth metal salts of citric acid, phytic acid or phosphoric acid and/or emulsifiers.

Emulsifiers or solubilizers which can be used are, for example, ascorbyl palmitate, polyglycerol esters of fatty acids, sorbitan esters of fatty acids, propylene glycol esters of fatty acids or lecithin.

The invention also relates to oily suspensions comprising, as disperse phase, solid preparations of at least one water-soluble, sparingly water-soluble or water-insoluble active compound suitable for the food and animal feed sectors or for pharmaceutical and cosmetic applications which are obtainable by
a) dissolving or dispersing at least one of the abovementioned active compounds in an aqueous molecular dispersion or colloidal dispersion of a proteinaceous protecting colloid,
b) flocculating the proteinaceous protecting colloid together with the active compound out of the dispersion and
c) separating off the flocculated solid from the water and any solvents additionally used and subsequently converting them into a dry powder.

In the case of the oily suspensions which comprise as disperse phase the above-described flocculated solids, the amount of the dispersion medium is generally from 50 to 99.9% by weight, preferably from 70 to 99.8% by weight, particularly preferably from 80 to 99.5% by weight, very particularly preferably from 90 to 99% by weight, based on the total mass of the oily dispersion.

The invention also relates to a process for producing carotenoid-containing oily suspensions, preferably oily suspensions comprising as active compound at least one carotenoid selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin, which comprises
a) grinding a dry powder comprising at least one carotenoid enclosed by one or more protecting colloids in at least one oil to a mean particle size of from 0.1 to 100 μm or
b) grinding a dry powder comprising at least one carotenoid enclosed by one or more protecting colloids without using a continuous phase to a mean particle size of from 0.1 to 100 μm and then suspending the ground particles in at least one oil or
c) grinding a carotenoid-containing suspension comprising, as solid, disperse phase, at least one carotenoid enclosed by one or more protecting colloids and, as dispersion medium, water or a mixture of water and a water-miscible solvent to a mean particle size of from 0.1 to 100 μm, then freeing the solid phase from the water or water/solvent mixture and suspending the resultant ground particles in at least one oil.

The grinding in all three process variants can be performed in a manner known per se using, for example, a ball mill. Depending on the mill type used, grinding is continued until the particles have a mean particle size, determined via Fraunhofer diffraction, D[4.3] of from 0.1 to 100 μm, preferably from 0.2 to 50 μm, particularly preferably from 0.5 to 30 μm, very particularly preferably from 0.8 to 20 μm, in particular from 1.0 to 10 μm.

Further details on grinding and the equipment used therefor may be found, inter alia, in Ullmann's Encyclopedia of Industrial Chemistry, Sixth Edition, 1999, Electronic Release, Size Reduction, Chapter 3.6.: Wet Grinding.

The water-miscible solvents used in process variant c) are especially water-miscible, thermally stable volatile solvents comprising only carbon, hydrogen and oxygen, such as alcohols, ethers, esters, ketones and acetals. Expediently, those solvents are used that are at least 10% water-miscible, have a boiling point below 200° C. and/or have less than 10 carbons. Particular preference is given to methanol, ethanol, n-propanol, isopropanol, 1,2-butanediol 1-methyl ether, 1,2-propanediol 1-n-propyl ether, tetrahydrofuran or acetone.

The water or water/solvent mixture can be separated off in process c) in a manner known per se, for example by distillation, if appropriate under reduced pressure. The distillation is generally carried out after grinding, but can also be carried out in the course of the grinding process.

In the inventive process, the oil used as dispersion medium is an edible oil liquid at 20° C., or a hard fat solid at 20° C.

Further details on the protecting colloids and dispersion media used are given in the description of the oily suspension already given at the outset.

The dry powder used for the grinding can generally be all solid preparations known from the prior art in which at least one carotenoid enclosed by a protecting colloid is present.

Preference is given to the dry powders produced as specified in EP-A-0 065 193, EP-A-0 832 569, DE-A-199 19 751, WO 98/26008, EP-A-0 937 412, WO 91/062292 and WO 94/19411.

The dry carotenoid powders described in EP-A-0 065 193 are obtainable by a process in which a carotenoid is briefly dissolved in a water-miscible organic solvent at elevated temperatures, the carotenoid is immediately precipitated from the resultant solution in colloidal dispersion form by rapid mixing with an aqueous solution of a protecting colloid and the resultant dispersion is converted into a dry powder.

According to EP-A-0 832 569, by heating the dispersion produced according to EP-A-0 065 193 at a temperature from 40° C. to 90° C. and then spray-drying it, a dry carotenoid powder is obtained in which the active compound particles are substantially amorphous as shown by x-ray diffraction.

The dry powders described in DE-A-199 19 751 comprise at least one xanthophyll selected from the group consisting of astaxanthin, lutein and zeaxanthin which is embedded in a matrix of casein as protecting colloid.

The dry powders described in WO 98/26008 comprise at least one xanthophyll which is embedded in a matrix of a mixture of low-molecular-weight and high-molecular-weight protecting colloids.

EP-A-0 937 412 relates to pulverulent carotenoid preparations obtainable by a) suspending a carotenoid in a water-immiscible solvent, in the presence or absence of an antioxidant and/or oil; b) heating this suspension to a temperature in the range from 100 to 250° C.; c) mixing the solution obtained according to b) with an aqueous protecting colloid solution at a temperature from 20 to 100° C.; d) separating off the organic solvent and converting the dispersion into a dry powder.

The dry powders disclosed in WO 91/062292 are obtainable by grinding the carotenoids in an aqueous protecting colloid solution and subsequently spray-drying the ground aqueous carotenoid suspension.

In WO 94/19411, crystalline carotenoids are ground in the presence of an aqueous protecting colloid solution, converted into an amorphous modification by short-time heating to the melting point, and then spray-dried.

For further details on the production of these dry powders, see the descriptions of the abovementioned publications.

The dry carotenoid powders used for producing the inventive oily suspensions, in addition to the protecting colloids, can comprise other aids such as plasticizers, emulsifiers and/or stabilizers.

The plasticizers used are sugars or sugar alcohols, for example sucrose, glucose, lactose, invert sugar, sorbitol, mannitol or glycerol.

The ratio of protecting colloid and plasticizer to carotenoid is generally selected in such a manner that the dry powder comprises from 0.5 to 65% by weight, preferably from 1 to 25% by weight, of carotenoid, from 10 to 50% by weight, preferably from 15 to 35% by weight, of a protecting colloid, from 20 to 70% by weight, preferably from 30 to 60% by weight, of a plasticizer, all percentages based on the dry mass of the powder, with or without minor amounts of a stabilizer.

To increase the stability of the carotenoids against oxidative degradation, it can be advantageous to add from 0 to 10% by weight, preferably from 0.5 to 7.5% by weight, based on the total amount of the dry powders, of one or more stabilizers such as α-tocopherol, t-butylated hydroxytoluene, t-butylated hydroxyanisole, ascorbic acid or ethoxyquin.

Emulsifiers can be, for example, ascorbyl palmitate, polyglycerol esters of fatty acids, sorbitan esters of fatty acids, propylene glycol esters of fatty acids or lecithin at a concentration of from 0 to 200% by weight, preferably from 5 to 150% by weight, particularly preferably from 10 to 80% by weight, based on the carotenoids in the dry powder.

In the case of a mixture of carotenoids, in the inventive grinding process it is possible to grind all of the components used in the suspension as a total mixture. However, each carotenoid to be ground can also be ground individually at high concentration in the oil to be used. The final preparation is then produced by mixing the respective individual suspensions.

The inventive oily suspensions can be diluted to the respective service concentration before use by adding fats or oils. They can be diluted, for example, with stirring at elevated temperatures, for example from 30 to 80° C.

The abovementioned suspensions are suitable, inter alia, as additive to animal feeds and food preparations or mixed feed, as compositions for producing pharmaceutical and cosmetic preparations and for producing food supplement preparations in the human and animal sectors.

Preferably, the suspensions may be used as feed additives in animal nutrition, for example by incorporation into feed pellets during extrusion or for application or spraying onto feed pellets.

The use as feed additives is performed in particular by direct spraying of the inventive suspensions, with or without dilution with oils, for example onto animal feed pellets in what is termed post-pelleting application.

A preferred embodiment of the spraying process is that the feed pellets are charged with the oily suspension under reduced pressure.

Examples of this are found, inter alia, in GB-A-2 232 573 and in EP-A-0 556 883.

Typical fields of application in the food sector are, for example, vitaminization and coloring of drinks, milk products such as yogurt, flavored milk drinks or dairy ice cream, and of pudding powders, egg products, baking mixes and confectionery.

In the cosmetics sector, the oily suspensions can be used, for example, for decorative body care products, for example in the form of a cream, a lotion, as lipsticks or make-up.

The invention further relates to food supplements, animal feeds, foods and pharmaceutical and cosmetic preparations which contain the oily suspensions described at the outset.

The invention preferably relates to animal feeds, in particular feed pellets, which are charged with the suspensions.

Food supplement preparations and pharmaceutical preparations which comprise the inventive suspension are, inter alia, tablets, dragées and, preferably, hard and soft gelatin capsules.

Cosmetic preparations which can comprise the inventive suspensions are, for example, preparations which can be applied topically, in particular decorative body care products such as lipsticks, face make-up in the form of a cream and lotions.

In the case of the active compounds which absorb UV light described at the outset (light screens), the inventive light-screen-containing solid preparations and the oily dispersions produced therefrom are also suitable as photostable UV filters in cosmetic and pharmaceutical preparations to protect human skin or human hair from solar radiation or from artificial light that has a high UV content, alone or together with compounds which are known for cosmetic or pharmaceutical preparations and absorb in the UV range. The cosmetic and pharmaceutical preparations as such are also obviously stabilized at the same time in order to remain active for as long as possible.

Therefore, the present invention also relates to light-screen-containing cosmetic and pharmaceutical preparations for protecting human skin or human hair from UV light in the range from 280 to 400 nm which comprise, in a cosmetically or pharmaceutically suitable carrier, active amounts of a formulation of sparingly water-soluble or water-insoluble organic UV filter substances as photostable UV filters, alone or together with compounds absorbing in the UVA and UVB ranges which are known per se for cosmetic and pharmaceutical preparations, in which the formulations are the inventive solid preparations mentioned at the outset or the oily dispersions produced therefrom.

The amount of sparingly water-soluble or water-insoluble organic UV filter substance in the form of the inventive formulations which is used in the cosmetic and pharmaceutical preparations is in the range from 0.05 to 20% by weight, preferably from 0.1 to 10% by weight, particularly preferably in the range from 1 to 7% by weight, based on the total amount of the cosmetic and pharmaceutical preparation.

The light-screen-containing cosmetic and pharmaceutical preparations are generally based on a carrier which comprises at least one oil phase. However, preparations solely on an aqueous basis are also possible. Therefore, compositions which come into consideration are oils, oil-in-water and water-in-oil emulsions, creams and pastes, protective lipstick compositions or fat-free gels.

Emulsions which come into consideration are, inter alia, also O/W macroemulsions, O/W microemulsions or O/W/O emulsions comprising amino-substituted hydroxybenzophenones of the formula I in disperse form, the emulsions being obtainable by phase-inversion technology, according to DE-A-197 26 121.

Customary cosmetic aids which can come into consideration as additives are, for example, coemulsifiers, fats and waxes, stabilizers, thickeners, biogenic active compounds, film-forming agents, perfumes, dyes, luster agents, preservatives, pigments, electrolytes (for example magnesium sulfate) and pH regulators. Coemulsifiers which come into consideration are preferably known W/O emulsifiers and in addition also O/W emulsifiers, for example polyglycerol esters, sorbitan esters or partially esterified glycerides. Typical examples of fats are glycerides; waxes are, inter alia, beeswax, paraffin wax or microwaxes, possibly in combination with hydrophilic waxes. Stabilizers which can be used are metal salts of fatty acids, for example magnesium stearate, aluminum stearate and/or zinc stearate. Suitable thickeners are, for example, crosslinked polyacrylic acids and their derivatives, polysaccharides, in particular xanthan gum, guar gum, agar, alginates and tyloses, carboxymethylcellulose and hydroxyethylcellulose, in addition fatty alcohols, monoglycerides and fatty acids, polyacrylates, polyvinyl alcohol and polyvinylpyrrolidone. Biogenic active compounds are, for example, plant extracts, protein hydrolysates and vitamin complexes. Customary film-forming agents are, for example, hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Luster agents which come into consideration are, for example, glycol distearate esters such as ethylene glycol distearate, but also fatty acids and fatty acid monoglycol esters. Dyes which can be used are the substances which are approved and suitable for cosmetic purposes, as compiled, for example, in the publication "Kosmetische Färbemittel" [Cosmetics Dyes] of the Farbstoffkommission der Deutschen Forschungsgemeinschaft [Dye Commission of the German Research Association], published by Verlag Chemie, Weinheim, 1984. These dyes are usually used at a concentration of from 0.001 to 0.1% by weight, based on the total mixture.

An additional content of antioxidants is generally preferred. Thus all antioxidants which are suitable or customary for cosmetic and/or dermatological applications can be used as favorable antioxidants.

Advantageously the antioxidants are selected from the group consisting of amino acids (for example glycine, histidine, tyrosine, tryptophan) and their derivatives, imidazoles (for example urocanic acid) and their derivatives, peptides such as D,L-carnosine, D-carnosine, L-carnosine and their derivatives (for example anserine), carotenoids, carotenes (for example β-carotene, lycopene) and their derivatives, chlorogenic acid and its derivatives, lipoic acid and its derivatives (for example dihydrolipoic acid), aurothioglucose, propylthiouracil and other thiols (for example thiorodoxin, glutathione, cysteine, cystine, cystamine and their glycosyl, N-acetyl, methyl, ethyl, propyl, amyl, butyl, and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulfoximine compounds (for example buthionine sulfoximines, homocysteine sulfoximines, buthionine sulfones, penta-, hexa- and heptathionine sulfoximine) in very low acceptable dosages (for example pmol to µmol/kg), in addition (metal)chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA and its derivatives, unsaturated fatty acids and their derivatives (for example γ-linolenic acid, linoleic acid, oleic acid), folic acid and its derivatives, ubiquinone and ubiquinol and their derivatives, vitamin C and its derivatives (for example ascorbyl palmitate, Mg ascorbyl phosphate, ascorbyl acetate), tocopherol and derivatives (for example vitamin E acetate, tocotrienol), vitamin A and derivatives (vitamin A palmitate) and coniferyl benzoate of benzoin resin, rutic acid and its derivatives, α-glycosylrutin, ferulic acid, furfurylideneglucitol, carnosine, butylated hydroxytoluene, butylated hydroxyanisole, nordihydroguaiac resin acid, nordihydroguaiaretic acid, trihydroxybutyrophenone, uric acid and its derivatives, mannose and its derivatives, zinc and its derivatives (for example ZnO, $ZnSO_4$), selenium and its derivatives (for example selenomethionin), stilbenes and their derivatives (for example stilbene oxide, trans-stilbene oxide).

The amount of the abovementioned antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or its derivatives are the antioxidant or antioxidants, it is advantageous to choose their respective concentrations from the range from 0.001 to 10% by weight, based on the total weight of the formulation.

If vitamin A and/or its derivatives or carotenoids are the antioxidant or antioxidants, it is advantageous to choose their respective concentration from the range from 0.001 to 10% by weight, based on the total weight of the formulation.

Customary oil components in cosmetics are, for example, paraffin oil, glyceryl stearate, isopropyl myristate, diisopropyl adipate, 2-ethylhexanoic acid cetyl stearyl ester, hydrogenated polyisobutene, vaseline, caprylic acid/capric acid triglycerides, microcrystalline wax, lanolin and stearic acid.

The total amount of aids and additives can be from 1 to 80, preferably from 6 to 40% by weight, and the nonaqueous portion ("active substances") can be from 20 to 80, preferably from 30 to 70% by weight, based on the media. The medium can be prepared in a manner known per se, that is to say, for example, by hot, cold, hot-hot/cold or PIT emulsification. This is a purely mechanical process: no chemical reaction takes place.

Such sunscreen preparations can therefore be in liquid, paste or solid form, for example as water-in-oil creams, oil-in-water creams and lotions, aerosol foam creams, gels, oils, fat sticks, powders, sprays or aqueous alcoholic lotions.

Finally, other substances which absorb in the UV range and are known per se can be used conjointly, provided that they are stable in the overall system of the combination of UV filters to be used according to the invention.

The majority of the light screens in the cosmetic and pharmaceutical preparations serving to protect the human epidermis consist of compounds which absorb UV light in the UVB region, that is to say in the range from 280 to 320 nm. For example, the content of the UVA absorbers to be used according to the invention is from 10 to 90% by weight, preferably from 20 to 50% by weight, based on the total amount of UVB and UVA absorbing substances.

Any UVA and UVB filter substances come into consideration as UV filter substances which are employed in combination with the formulations to be used according to the invention. Examples are:

| No. | Substance | CAS No. (=acid) |
|---|---|---|
| 1 | 4-aminobenzoic acid | 150-13-0 |
| 2 | 3-(4'-trimethylammonium)benzylidenebornan-2-one methyl sulfate | 52793-97-2 |
| 3 | 3,3,5-trimethylcyclohexylsalicylate (homosalatum) | 118-56-9 |
| 4 | 2-hydroxy-4-methoxybenzophenone (oxybenzonum) | 131-57-7 |
| 5 | 2-phenylbenzimidazole-5-sulfonic acid and its potassium, sodium and triethanolamine salts | 27503-81-7 |
| 6 | 3,3'-(1,4-phenylenedimethyne)bis(7,7-dimethyl-2-oxobicyclo[2.2.1]heptane-1-methanesulfonic acid) and its salts | 90457-82-2 |
| 7 | 4-bis(polyethoxy)aminobenzoic acid polyethoxyethyl ester | 113010-52-9 |
| 8 | 4-dimethylaminobenzoic acid 2-ethylhexyl ester | 21245-02-3 |
| 9 | salicylic acid 2-ethylhexyl ester | 118-60-5 |
| 10 | 4-methoxycinnamic acid 2-isoamyl ester | 71617-10-2 |
| 11 | 4-methoxycinnamic acid 2-ethylhexyl ester | 5466-77-3 |
| 12 | 2-hydroxy-4-methoxybenzophenone-5-sulfonic acid (sulisobenzonum) and the sodium salt | 4065-45-6 |
| 13 | 3-(4'-sulfo)benzylidenebornan-2-one and salts | 58030-58-6 |
| 14 | 3-benzylidenebornan-2-one | 16087-24-8 |
| 15 | 1-(4'-isopropylphenyl)-3-phenylpropane-1,3-dione | 63260-25-9 |
| 16 | 4-isopropylbenzyl salicylate | 94134-93-7 |
| 17 | 2,4,6-trianilino-(o-carbo-2'-ethyl-1'-hexyloxy)-1,3,5-triazine | 88122-99-0 |
| 18 | 3-imidazol-4-ylacrylic acid and its ethyl ester | 104-98-3 |
| 19 | 2-cyano-3,3-diphenylacrylic acid ethyl ester | 5232-99-5 |
| 20 | 2-cyano-3,3-diphenylacrylic acid 2'-ethylhexyl ester | 6197-30-4 |
| 21 | menthyl o-aminobenzoates or: 5-methyl-2-(1-methylethyl)-2-aminobenzoates | 134-09-8 |
| 22 | glyceryl p-aminobenzoate or: 4-aminobenzoic acid 1-glyceryl ester | 136-44-7 |
| 23 | 2,2'-dihydroxy-4-methoxybenzophenone (dioxybenzones) | 131-53-3 |
| 24 | 2-hydroxy-4-methoxy-4-methylbenzophenone (mexo-none) | 1641-17-4 |
| 25 | triethanolamine salicylate | 2174-16-5 |
| 26 | dimethoxyphenylglyoxalic acid or: 3,4-dimethoxyphenylglyoxalic acid sodium | 4732-70-1 |
| 27 | 3-(4'-sulfo)benzylidenebornan-2-one and its salts | 56039-58-8 |
| 28 | 4-tert-butyl-4'-methoxydibenzoylmethane | 70356-09-1 |
| 29 | 2,2',4,4'-tetrahydroxybenzophenone | 131-55-5 |
| 30 | 2,2'-methylenebis[6(2H-benzotriazol-2-yl)-4-(1,1,3,3-tetramethylbutyl)phenol] | 103597-45-1 |
| 31 | 2,2'-(1,4-phenylene)bis-1H-benzimidazole-4,6-disulfonic acid, Na salt | 180898-37-7 |
| 32 | 2,4-bis[4-(2-ethylhexyloxy)-2-hydroxy]phenyl-6-(4-methoxyphenyl)-(1,3,5)-triazine | 187393-00-6 |
| 33 | 3-(4-methylbenzylidene)camphor | 36861-47-9 |
| 34 | 4-bis(polyethoxy)paraaminobenzoic acid polyethoxyethyl ester | 113010-52-9 |
| 35 | 2,4-dihydroxybenzophenone | 131-56-6 |
| 36 | 2,2'-dihydroxy-4,4'-dimethoxybenzophenone-5,5'-disodium sulfonate | 3121-60-6 |

Polymeric or polymer-bound filter substances can also be used according to the invention.

The inventive cosmetic and dermatological preparations can advantageously also comprise inorganic pigments based on metal 10 oxides and/or other sparingly water-soluble or water-insoluble metal compounds, in particular the oxides of titanium ($TiO_2$), zinc (ZnO), iron (for example $Fe_2O_3$), zirconium ($ZrO_2$), silicon ($SiO_2$), manganese (for example MnO), aluminum ($Al_2O_3$), cerium (for example $Ce_2O_3$), mixed oxides of the corresponding metals and mixtures of such oxides. Particularly preferably, such pigments are based on $TiO_2$ and ZnO.

It is particularly advantageous in the present invention, although not obligatory, if the inorganic pigments are present in hydrophobic form, that is to say they are surface-treated in a water-repellent manner. This surface treatment can be that the pigments are provided with a thin hydrophobic coating in a manner known per se, as described in DE-A-33 14 742.

To protect human hair from UV radiation, the inventive light screen formulations can be incorporated into shampoos, lotions, gels, hairsprays, aerosol foam creams or emulsions at concentrations of from 0.1 to 10% by weight, preferably from 1 to 7% by weight. The respective formulations can be used here, inter alia, for washing, dyeing or styling hair.

The formulations to be used according to the invention are generally distinguished by a particularly high absorption capacity in the UVA radiation region with a sharp band structure.

In addition, they are readily soluble in cosmetic oils and may be readily incorporated into cosmetic formulations. The emulsions produced using the formulations are distinguished particularly by their high stability, the formulations I themselves by their high photostability, and the preparations produced therewith by their pleasant feel on the skin.

The UV filter action of the inventive formulations can also be utilized to stabilize active compounds and aids in cosmetic and pharmaceutical formulations.

The inventive preparations are distinguished by a particularly high absorption capacity in the UVB radiation range with sharp band structure and high light screen factors.

In particular, the high light screen factor of the preparations, which was measured even at low concentrations of UV-absorbing active compounds, was surprising.

In the examples below, the procedure of the inventive process is described in more detail.

EXAMPLE 1

Astaxanthin Dry Powder 45 g of crystalline astaxanthin were suspended at room temperature in 375 g of an azeotropic isopropanol/water mixture. This active compound suspension was then heated to 96° C. and, at a flow rate of 2.1 kg/h, continuously mixed with further isopropanol/water azeotrope at a temperature of 227° C. and a flow rate of 2.7 kg/h, the astaxanthin dissolving at a mixture temperature of 169° C. and a pressure of 60 bar. The resultant active compound solution was then mixed at a flow rate of 56.1 kg/h with an aqueous phase consisting of a solution of 80 g of Na caseinate in 12 l of distilled water in which the pH had been set to 8.0 using 18 mL of 1 M NaOH.

The nanoparticulate active compound particles formed during the mixing had a particle size of 100 nm in the isopropanol/water mixture. The active compound dispersion was then set to pH 4.8 using 1 M HCl, so that the active compound/caseinate particles were flocculated out. After the flocculated particles were filtered off via a filter bag and subsequent freeze-drying, a dry powder having an astaxanthin content of 36% by weight was obtained.

EXAMPLE 2

Astaxanthin Dry Powder 50 g of crystalline astaxanthin and 5.6 g of ethoxyquin were suspended at room temperature in 416 g of an azeotropic isopropanol/water mixture. The active compound suspension was then heated to 97° C. and, at a flow rate of 2.1 kg/h, continuously mixed with further isopropanol/water azeotrope at a temperature of 216° C. and a flow rate of 2.7 kg/h, the astaxanthin dissolving at a mixture temperature of 169° C. and a pressure of 60 bar. The active compound solution was then mixed at a flow rate of 55.6 kg/h with an aqueous phase consisting of a solution of 23.3 g of Na caseinate in 14 l of distilled water in which the pH had been set to 8.3 using 5 mL of 1 M NaOH.

The active compound particles formed during the mixing had a particle size of 116 nm in the isopropanol/water mixture. This active compound dispersion was then set to pH 4.8 using 1 M HCl, so that the active compound/caseinate particles were flocculated out. The suspension was then filtered via a filter bag and the filter cake was dried. The resultant solids had an astaxanthin content of 62% by weight.

EXAMPLE 3

Lycopene Dry Powder 45 g of crystalline lycopene, 3.6 g of palmitic acid and 6.6 g of tocopherol were suspended at room temperature in 388 g of an azeotropic isopropanol/water mixture. The active compound suspension was then heated to 94° C. and, at a flow rate of 2.0 kg/h, continuously mixed with further isopropanol/water azeotrope at a temperature of 206° C. and a flow rate of 3.3 kg/h, the lycopene dissolving at a mixture temperature of 171° C. and a pressure of 63 bar. The resultant active compound solution was mixed at a flow rate of 33.8 kg/h with an aqueous phase consisting of a solution of 80 g of Na caseinate in 7 l of distilled water in which the pH had been set to 8.0 using 19 mL of 1 M NaOH.

The active compound particles formed during the mixing had a particle size of 125 nm in the isopropanol/water mixture. The active compound dispersion was then set to pH 4.8 using 1 M HCl, so that the active compound/caseinate particles were flocculated out. The suspension was then filtered through a filter bag and freeze-dried. The dried filter cake had a lycopene content of 32% by weight.

EXAMPLE 4

β-Carotene Dry Powder 45 g of β-carotene, 3.6 g of ascorbyl palmitate and 6.6 g of tocopherol were suspended at room temperature in 388 g of an azeotropic isopropanol/water mixture. The active compound suspension was then heated to 96° C. and, at a flow rate of 2.1 kg/h, continuously mixed with further isopropanol/water azeotrope at a temperature of 210° C. and a flow rate of 3.0 kg/h, the β-carotene dissolving at a mixture temperature of 170° C. and a pressure of 62 bar. The active compound solution was then mixed at a flow rate of 35.5 kg/h with an aqueous phase consisting of a solution of 80 g of Na caseinate in 7 l of distilled water in which the pH had been set to 8.0 using 18 mL of 1 M NaOH.

The active compound particles formed during the mixing had a particle size of 138 nm in the isopropanol/water mixture. This active compound dispersion was then set to pH 4.8 using 1 M HCl, so that the active compound/caseinate particles were flocculated out. The suspension was then filtered through a filter bag. The filter cake was then dried via freeze-drying. The dried filter cake had a β-carotene content of 32% by weight.

EXAMPLE 5

Astaxanthin Dry Powder (Acid Procedure)

45 g of crystalline astaxanthin and 4.5 g of vanillin were suspended at room temperature in 375 g of an azeotropic isopropanol/water mixture. The active compound suspension was then heated to 98° C. and, at a flow rate of 2.1 kg/h, continuously mixed with further isopropanol/water azeotrope at a temperature of 230° C. and a flow rate of 2.8 kg/h, the astaxanthin dissolving at a mixture temperature of 171° C. and a pressure of 61 bar. The active compound solution was then mixed at a flow rate of 55.2 kg/h with an aqueous phase consisting of a solution of 80 g of Na caseinate (Lacto Bretagne Associés) in 12,000 g of distilled water in which the pH had been set to 2.9 using 88 g of 1 M HCl.

The active compound particles formed during the mixing had a particle size of 1.2 µm in the isopropanol/water mixture. The active compound dispersion was then set to pH 4.8 using 1 M NaOH, so that the active compound/caseinate particles were flocculated out. The suspension was then filtered through a filter bag. The filter cake was then dried via freeze-drying. The dried filter cake had an astaxanthin content of 35% by weight.

EXAMPLE 6

Grinding of Lycopene With Caseinate 3.3 g of crystalline lycopene, 2.5 g of Na caseinate and 0.33 g of ascorbyl palmitate were suspended at room temperature in 40 g of deionized water and the pH of the suspension was made alkaline using 3 g of 1 M NaOH. The active compound suspension, together with approximately 200 g of zirconium oxide ceramic grinding beads having a diameter of 1 mm, was then dispersed on a Red Devil mixer in a 100 ml glass flask. After a grinding time of 3, 6 and 12 hours, samples were taken in order to characterize the progress of the grinding. The mean particle sizes at these times were 651 nm with 67% variance, 487 nm with 50% variance and 494 nm with 55% variance. The pH of the final sample was 7.7 at an E1/1 value of 136.

This active compound dispersion was then set to pH 4.8 using 1 M HCl, so that the active compound/caseinate particles were flocculated out. After filtration through a filter bag, the filter cake was then freeze-dried.

EXAMPLE 7

Astaxanthin Suspension in Oil

To produce a highly concentrated oily astaxanthin suspension, 20 g of the astaxanthin dry powder obtained according to Example 2 were suspended together with 1.0 g of ethoxyquin, 1.0 g of preservative (BHT) and 4.0 g of emulsifier (Span 65, Sigma) in 100 g of neutral oil (Delios SK, Grünau) for 5 minutes using an Ultra Turrax. The resultant oil suspension which was stable to sedimentation had an astaxanthin content of 8.5% by weight, with a secondary particle size of 34 μm.

EXAMPLE 8

Astaxanthin Suspension in Oil

Two kilograms of a mixture of 30% by weight of an astaxanthin-containing dry powder (Lucantin® Pink 10% strength, BASF AG) and 70% by weight of soybean oil were stirred with a vane stirrer until the suspension was homogeneous. The mixture was then transferred to a stirrable reservoir from which the suspension was transported by means of a peristaltic pump via a continuous ball mill (Dyno Mill KDL Spezial). The grinding vessel of the ball mill was packed with 400 g of glass balls (diameter 800–1200 μm). The finely divided suspension exiting from the mill was collected and measured using a particle size measuring apparatus (Malvern Mastersizer). The grinding operation was repeated until 90% of the suspended particles had a particle size less then 10 μm [D(0.9)<10 μm]. This corresponded to a mean particle size D[4.3] of 5.2 μm.

After separating off the milling bodies, part of the suspension was diluted with 10 times the amount of the oil used and allowed to stand for 12 h. Neither the undiluted nor the diluted suspension showed sedimentation phenomena over this period.

We claim:

1. A process for producing solid preparations of at least one water-soluble, sparingly water-soluble or water-insoluble active compound suitable for the food and animal feed sectors or for pharmaceutical and cosmetic applications by
   a) dissolving or dispersing at least one of the abovementioned active compounds in an aqueous molecular dispersion or colloidal dispersion of casein or a caseinate as proteinaceous protecting colloid,
   b) flocculating the proteinaceous protecting colloid together with the active compound out of the dispersion by setting the pH of the dispersion to a value in a range of from 4.0 to 5.5, and
   c) separating off the flocculated solid from the water and any solvents additionally used and subsequently converting them into a dry powder.

2. A process as claimed in claim 1 for producing solid preparations of at least one sparingly water-soluble or water-insoluble active compound suitable for the food and animal feed sectors or for pharmaceutical and cosmetic applications, wherein, in process step a), at least one of the abovementioned active compounds is dispersed in an aqueous molecular dispersion or colloidal dispersion of a proteinaceous protecting colloid.

3. A process as claimed in claim 2, wherein the dispersion step a) is the production of a suspension of at least one solid active compound in an aqueous molecular dispersion or colloidal dispersion of a proteinaceous protecting colloid.

4. A process as claimed in claim 3, wherein the suspension produced in process step a) is ground before the flocculation.

5. A process as claimed in claim 2, wherein the dispersion in stage a) comprises the following steps:
   $a_1$) dissolving one or more sparingly water-soluble or water-insoluble active compounds in a water-miscible organic solvent or a mixture of water and a water-miscible organic solvent or
   $a_2$) dissolving one or mote sparingly water-soluble or water-insoluble active compounds in a water-immiscible organic solvent and
   $a_3$) mixing the solution obtained by $a_1$) or $a_2$) with an aqueous molecular dispersion or colloidal dispersion of casein or a caseinate as proteinaceous protecting colloid, the hydrophobic phase of the active compound being produced as nanodisperse phase.

6. A process as claimed in claim 5, wherein, when process step $a_2$) is being performed, the water-immiscible solvent is distilled off before flocculating the protecting colloid.

7. A process as claimed in claim 1, which involves the production of carotenoid-containing dry powders.

8. A process as claimed in claim 7 for producing dry powders comprising carotenoids selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin.

9. A process as claimed in claim 7, wherein
   a) one or more carotenoids are dissolved in a water-miscible organic solvent, or a mixture of water and a water-miscible organic solvent, at temperatures above 30° C.,
   b) the resultant solution is mixed with an aqueous solution of casein or caseinate,
   c) the casein or caseinate is flocculated out of the dispersion together with the carotenoid at a pH of the dispersion in a range of from 4.0 to 5.5,
   d) the flocculated solid is separated off from the water and solvent and dried.

10. A solid preparation of at least one water-soluble, sparingly water-soluble or water-insoluble active compound suitable for the food and animal feed sectors or for pharmaceutical and cosmetic applications and obtainable by a process as defined in claim 1.

11. A solid preparation as claimed in claim 10 comprising at least one sparingly water-soluble or water-insoluble active compound suitable for the food and animal feed sectors or for pharmaceutical and cosmetic applications.

12. A solid preparation as claimed in claim 10 having an active compound content of from 0.1 to 80% by weight.

13. A solid preparation as claimed in claim 11 which is a carotenoid-containing dry powder.

14. A dry powder as claimed in claim 13 comprising carotenoids selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin.

15. An oily suspension comprising, as disperse phase, solid preparations of at least one water-soluble, sparingly water-soluble or water-insoluble active compound suitable for the food and animal feed sectors or for pharmaceutical and cosmetic applications which are obtainable by a) dissolving or dispersing at least one of the abovementioned active compounds in an aqueous molecular dispersion or colloidal dispersion of casein or a caseinate as proteinaceous protecting colloid, b) flocculating the proteinaceous protecting colloid together with the active compound out of the dispersion by setting the pH of the dispersion to a value in a range of from 4.0 to 5.5, and c) separating off the flocculated solid from the water and any solvents additionally used and subsequently converting them into a dry powder.

16. An oily suspension as claimed in claim 15 having an active compound content of from 0.1 to 50% by weight, based on the total amount of oily suspension.

17. An oily suspension as claimed in claim 15 comprising as active compound at least one carotenoid selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin.

18. A process for producing a carotenoid-containing oily suspension comprising, as disperse phase, at least one carotenoid selected from the group consisting of astaxanthin, β-carotene, β-apo-8'-carotenal, β-apo-8'-carotenic acid ethyl ester, canthaxanthin, citranaxanthin, echinenone, lutein, lycopene and zeaxanthin, which carotenoid is enclosed by one or more protecting colloids, with the proviso that the oily suspension comprises no water-soluble vitamins, which process comprises a) grinding a dry powder comprising the at least one carotenoid enclosed by one or more protecting colloids in at least one oil to a mean particle size of from 0.1 to 100 μm or b) grinding a dry powder comprising the at least one carotenoid enclosed by one or more protecting colloids without using a continuous phase to a mean particle size of from 0.1 to 100 μm and then suspending the ground particles in at least one oil or c) grinding a carotenoid-containing suspension comprising, as solid phase, the at least one carotenoid enclosed by one or more protecting colloids and, as dispersion medium, water or a mixture of water and a water-miscible solvent to a mean particle size of from 0.1 to 100 μm, then freeing the solid phase from the water or water/solvent mixture and suspending the resultant ground particles in at least one oil.

19. A process as claimed in claim 18, wherein the oil is an edible oil liquid at 20° C.

20. A process as claimed in claim 18, wherein the oil is a hard fat solid at 20° C.

21. A process for producing solid preparations of at least one water-soluble, sparingly water-soluble or water insoluble active compound suitable for the food and animal feed sectors or for pharmaceutical and cosmetic applications comprising the following steps:

$a_1$) preparing an active compound suspension by suspending at least one of the abovementioned active compounds with a proteinaceous protecting colloid in a solvent, $a_2$) grinding the active compound suspension, b) flocculating out active compound-proteinaceous protecting colloid particles, and c) separating off the active compound-proteinaceous protecting colloid particles from water and any solvents used, and subsequently converting the particles into a dry powder.

\* \* \* \* \*